United States Patent
Kiefer et al.

(10) Patent No.: US 10,436,867 B2
(45) Date of Patent: Oct. 8, 2019

(54) METHOD AND COMPUTER FOR AUTOMATIC CHARACTERIZATION OF LIVER TISSUE FROM MAGNETIC RESONANCE IMAGES

(71) Applicant: Siemens Healthcare GmbH, Erlangen (DE)

(72) Inventors: Berthold Kiefer, Erlangen (DE); Marcel Dominik Nickel, Herzogenaurach (DE); Stephan Kannengiesser, Wuppertal (DE)

(73) Assignee: Siemens Healthcare GmbH, Erlangen (DE)

( * ) Notice: Subject to any disclaimer, the term of this patent is extended or adjusted under 35 U.S.C. 154(b) by 94 days.

(21) Appl. No.: 15/613,563

(22) Filed: Jun. 5, 2017

(65) Prior Publication Data
US 2017/0350952 A1 Dec. 7, 2017

(30) Foreign Application Priority Data
Jun. 6, 2016 (DE) .......... 10 2016 209 885

(51) Int. Cl.
*G01R 33/50* (2006.01)
*G01R 33/341* (2006.01)
(Continued)

(52) U.S. Cl.
CPC .......... *G01R 33/50* (2013.01); *A61B 5/055* (2013.01); *A61B 5/4244* (2013.01);
(Continued)

(58) Field of Classification Search
None
See application file for complete search history.

(56) References Cited

U.S. PATENT DOCUMENTS

| 5,003,979 A | 4/1991 | Merickel et al. |
| 2007/0247153 A1* | 10/2007 | Yu .......... G01N 24/08 324/307 |

(Continued)

FOREIGN PATENT DOCUMENTS

| CN | 101001569 A | 7/2007 |
| CN | 105431089 A | 3/2016 |
| CN | 105608681 A | 5/2016 |

OTHER PUBLICATIONS

Bashir et al. "Hepatic MR imaging for in vivo differentiation of steatosis, iron deposition and combined storage disorder; Single-ratio in/opposed phase analysis vs. dual-ratio Dixon discrimination," European Journal of Radiology, vol. 81, pp. 101-109 (2012).

(Continued)

*Primary Examiner* — Douglas X Rodriguez
(74) *Attorney, Agent, or Firm* — Schiff Hardin LLP (57) ABSTRACT

In a computer and a magnetic resonance method and apparatus for automatic characterization (classification) of liver tissue in a region of interest of a liver, at least one value tuple of the region of interest of the liver is acquired, the value tuple including at least one $T_1$ value determined from magnetic resonance images of the region of interest, or a reciprocal value thereof, and a $T_2$ or $T_2^*$ value or a reciprocal value thereof. The value tuple is transferred into a multidimensional parameter space and the characterization of the liver tissue is then performed on the basis of the position of the value tuple in the parameter space.

9 Claims, 3 Drawing Sheets

(51) Int. Cl.
  *G01R 33/483* (2006.01)
  *G01R 33/56* (2006.01)
  *A61B 5/055* (2006.01)
  *A61B 5/00* (2006.01)

(52) U.S. Cl.
  CPC ......... *G01R 33/341* (2013.01); *G01R 33/483* (2013.01); *G01R 33/5608* (2013.01)

(56) References Cited

U.S. PATENT DOCUMENTS

| | | |
|---|---|---|
| 2008/0004521 A1 | 1/2008 | Hundley et al. |
| 2014/0330106 A1 | 11/2014 | Banerjee et al. |
| 2015/0025372 A1 | 1/2015 | Ghosh et al. |
| 2015/0301141 A1 | 10/2015 | Griswold et al. |

OTHER PUBLICATIONS

Banerjee et al. "Multiparametric magnetic resonance for the non-invasive diagnosis of liver disease," Journal of Hepatology, vol. 60, pp. 69-77 (2014).
Chinese Office Action Application No. 201710417133.2, dated Apr. 25, 2019 (with English-language translation).

\* cited by examiner

METHOD AND COMPUTER FOR AUTOMATIC CHARACTERIZATION OF LIVER TISSUE FROM MAGNETIC RESONANCE IMAGES

BACKGROUND OF THE INVENTION

Field of the Invention

The present invention relates to a method for the automatic characterization, preferably classification, of liver tissue in a region of interest of a liver of a living subject. The invention also relates to a characterization computer, in particular a classification computer, for the automatic characterization, preferably classification, of liver tissue on the basis of magnetic resonance images of the region of interest, and a magnetic resonance apparatus with such a characterization computer.

Description of the Prior Art

Liver disease is one of the most common causes of death. While the mortality rate for other diseases is falling, the incidence of liver disease is actually rising. One typical liver disease is hepatitis, which first causes inflammation that then changes to fibrosis and can later result in cirrhosis of the liver or liver cancer. Another problematic field is hemochromatosis (iron-storage disease) with which the body absorbs too much iron with the food. Here, once again, generally the liver is affected first and subsequently other organs, such as the pancreas or heart, are endangered. In the final stage, hemochromatosis can also result in cirrhosis of the liver or liver cancer. A further problem is the development of fatty liver disease.

Although, with usual precautionary checkups, a blood count generally also includes checks on various liver values, most liver diseases typically are only manifested at a later stage, and other symptoms also only occur once the disease has reached a significantly advanced stage. This greatly complicates treatment. In many cases, it is no longer possible to provide a cure.

Magnetic resonance scans are increasingly being used to obtain additional quantitative information about organs, such as the fat content. These values can then be used again as biomarkers for certain diseases. For example, like the blood count, in some circumstances, the values can also be used in clinical practice to determine the status of the disease or to monitor the course of treatment. Therefore, it would be desirable to be able to determine liver disease at a relatively early stage with the use of magnetic resonance images.

A disadvantage to doing so, however, is that generally the information about a specific disease is not contained in one single parameter that can be determined from the magnetic resonance images, but is presented in a combination of different parameters. It is also the case that different parameters can exert a mutual influence on one another. This relates to the determination of fibrosis in the liver. Although this can be identified by measurements using $T_1$ images (i.e. $T_1$-weighted images or by measuring the $T_1$ values), since longer $T_1$ relaxation times (spin-lattice relaxation times) can be indicative of more severe fibrosis, hepatic iron overload of the liver disadvantageously results in reduced $T_1$ relaxation times. The outcome of this can be that, in patients with both hepatic iron overload and fibrosis, the fibrosis is masked by the hepatic iron overload and thus neither of the two diseases can be determined by the $T_1$ measurement. Iron overload can also be indicated by measuring the $T_2$ or $T_2^*$ values (spin-spin relaxation times, wherein $T_2$ relates to spin-echo methods and $T_2^*$ to gradient-echo methods) or reciprocal values thereof.

To a certain extent, very experienced radiologists can also make assessments from individual analyses of the $T_1$ images and $T_2$ or $T_2^*$ images or the reciprocal images thereof. However, this is always heavily dependent upon the experience of the diagnosing physician in question.

Therefore, it is suggested in the article by Banerjee R. et al. "Multiparametric magnetic resonance for the non-invasive diagnosis of liver disease", Journal of Hepatology, 2014, Vol. 60, pages 69 to 77, that the $T_1$ values first be converted to "$cT_1$ values" (corrected $T_1$ values), wherein the hepatic iron overload is included in the correction by the use of the $T_2$ or $T_2^*$ values. These "$cT_1$ values" then permit assessments of the status of a possible fibrosis of the liver tissue.

SUMMARY OF THE INVENTION

An object of the present invention is to provide an alternatives simple method for the characterization of liver tissue, and a corresponding characterization computer with which it is possible in a simple way to automatically obtain suggestions for characterization or suggestions for classification, in particular for the degree of fibrosis of a liver.

The method according to the invention has at least the following method steps.

At least one value tuple of the region of interest of the liver is acquired that includes at least one $T_1$ value determined with the use of magnetic resonance images of the region of interest, or a reciprocal value thereof, and a $T_2$ or $T_2^*$ value or a reciprocal value thereof. Therefore, this $T_1$ value or the $T_2$ or $T_2^*$ value (or the reciprocal values) are the attributes of the tuple.

This value tuple is then transferred into a multidimensional, i.e. at least two-dimensional, parameter space, which, for example, correspondingly has at least one coordinate axis for the $T_1$ value and at least one coordinate axis for the $T_2$ or $T_2^*$ value (or in each case the reciprocal value thereof).

The characterization, preferably classification, of the liver tissue is then performed on the basis of the position of the value tuple in the multidimensional parameter space.

In this context, it is possible for a common value tuple to be determined for the entire region of interest. Similarly, as will be explained below, it is also possible to use several tuples for a region of interest, for example an individual value tuple for each image point—i.e. pixel or voxel—in the region of interest. In this context, there are various methods for determining a suggested characterization or suggested classification automatically from several value tuples or the positions thereof in the parameter space.

Therefore, the method according to the invention is ultimately used to generate a new multidimensional (or at least two-dimensional) parameter map from the different parameter maps, for example a $T_1$ image (also called a $T_1$ map) and a $T_2$ or $T_2^*$ image (also called a $T_2$ or $T_2^*$ map) or the reciprocal values thereof, by simple grouping of these values to form tuples, for example in each case for the individual image points in the position space or by the formation of combination values or combination-value tuples and positioning these tuples in a multidimensional space, which is spanned by the parameters $T_1$ and $T_2$ or $T_2^*$ or the reciprocal values thereof and optionally further coordinate axes for other parameters. In this, it is then possible to identify simple regions indicating certain conditions of the liver tissue. This permits a relatively early assessment at least before the assessment of the probability of a correct characterization, in particular classification, in the form of suggested characterizations or suggested classifications, which also enable less experienced people to make a reliable characterization or classification. In this context, a suggested characterization can include information on the (presumed) condition of the liver tissue, wherein a classification can include classification into certain, optionally freely definable, condition classes such as "No findings", "Grade X fibrosis", "Grade X cirrhosis" etc. In this context, with certain embodiments, (pseudo-) continuous characterization or gradual classification is also possible, i.e. wherein, for example, a quantitative value characterizing the liver tissue is disclosed, for example the part for which or degree to which a certain class or a certain condition has been achieved.

A characterization computer, preferably a classification computer, according to the invention is configured to implement these method steps.

The basic components of the characterization computer or classification computer according to the invention can be embodied as software components. However, in principle, particularly when fast calculations are required, some of these components can be implemented in the form of software-assisted hardware, for example FPGAs or the like. Similarly, the required interfaces can be embodied as software interfaces, for example when it is only a matter of transferring data from other software components. They can also be embodied as hardware-based interfaces, which are activated by suitable software.

The characterization computer or classification computer according to the invention can be implemented, for example, by the suitable software components on an image evaluation computer, which is independent of the actual magnetic resonance system, for example a workstation. Such a computer accepts the necessary parameter maps or image data, such as $T_1$-weighted image data and $T_2$ or $T_2^*$-weighted image data or reciprocal maps thereof, from a magnetic resonance scanner and/or from a memory in which the data are stored. However, in principle, the characterization computer or classification computer can be a part of the magnetic resonance system, for example embodied in the control computer thereof or in an evaluation station connected directly thereto, in order to perform the classification immediately after the scan. Accordingly, the acquisition of the value tuple can simply include the acceptance of the corresponding parameter maps or image data (such as $T_1$-weighted images, $T_2$ or $T_2^*$-weighted images, or reciprocal images or parameter maps), or can include the acquisition of the magnetic resonance data for the region of interest of the liver itself and the determination of the $T_1$ values or reciprocal values thereof and the $T_2$ or $T_2^*$ values or reciprocal values thereof of the image points in the region of interest on the basis of this raw data. In other words, the image reconstruction is then also part of the method according to the invention.

An extensively software-based implementation has the advantage that existing workstations or control computers can be easily retrofitted by a software update in order to operate in the inventive manner. This, the above object also is achieved by a non-transitory, computer-readable data storage medium encoded with programming instructions, which can be loaded directly into a memory of a workstation or a memory of a magnetic resonance system. The programming instructions (program code) cause the steps of the method according to the invention to be implemented when the program code is executed in the workstation or the control computer. In addition to the program code, the storage medium can optionally include additional items such as documentation and/or additional components, and also hardware-components, such as hardware keys (dongles etc.) to enable use of the software.

The computer-readable medium can be, for example a memory stick, a hard disk or some other transportable or permanently installed data medium. The computer can have, for example, one or more interacting microprocessors or the like.

According to the invention, a value tuple has at least two attributes, i.e. the $T_1$ value or a reciprocal value thereof and the $T_2$ or $T_2^*$ value or a reciprocal value thereof. Accordingly, the multidimensional parameter space is at least two-dimensional. Preferably, the value tuple additionally has a number of further values or attributes, i.e. further parameters are added to improve the suggested characterizations or suggested classifications.

Preferably, one of the values additionally included in the value tuple is a fat value. Such fat values can normally be determined without difficulty from the scan data since the majority of liver sequences, which can also be used to determine the $T_1$ or $T_2$ or $T_2^*$ values, are already designed so as to utilize a multi-gradient echo sequence. From this, it is possible to determine the fat content and the T2* value simultaneously.

Further parameters of interest suitable for the characterization of liver tissue are the rigidity of the tissue, which can be determined from elastography images, the ability to absorb contrast medium from contrast medium images and $T_1\rho$ values (spin-lattice relaxation time in the rotating coordinate system) from "spin-lock" sequences.

It is also possible to compile further parameters indirectly, for example on the basis of quantitative values or other available information. This includes structural values, such as a texture value (i.e. the nature of the tissue structure, for example rough, smooth, blurred etc.).

All these values can also be taken account of as additional values or attributes in the tuple. Such additional values then optionally enable even more reliable separation of the different regions which are indicative of certain conditions of the liver, since there can be a greater or more obvious spatial distance between the different conditions or the areas belonging thereto within the parameter spaces with higher dimensions.

Regardless of how many values or attributes of the value tuples or how many dimensions are included in the parameter space, there are different possibilities for performing the characterization or classification of the liver tissue on the basis of the position of the value tuple in the parameter space.

For example, this can be performed with reference to a boundary hyperplane of the parameter space. For example, the parameter space can be divided by the boundary hyperplane(s) into subspaces and, depending upon where the value tuple or tuples of the liver tissue to be characterized, in particular classified, are located, this indicates the condition of the liver tissue in question. In this context, a "hyperplane" should be understood in the mathematical sense of any type of plane within the multidimensional parameter space (i.e. with an n-dimensional space therefore an n−1-dimensional subspace). For example, such a hyperplane in the respective space can also be curved or angled etc. This can also in particular also entail a volume interface enclosing a specific subregion within the multidimensional parameter space, for example a spherical surface. The characterization, in particular classification, of the liver tissue on the basis of the position of the value tuple can then be performed simply in that a decision is taken as to whether the value tuple is located inside or outside the space enclosed by the surface.

In a further embodiment, which can be combined with the first-described embodiment of boundary hyperplanes, the characterization, in particular the classification, of the liver tissue is made on the basis of the position of the value tuple with reference to at least one cluster of reference value tuples in the multidimensional parameter space. In this context, the reference value tuple can have been determined with the aid of previous examinations on other patients and stored in a suitable manner in databases or the like. The clusters of reference tuples then, for example, in each case represent specific classes. It is possible to construct a corresponding dataset in that a plurality of patients with different liver conditions, but for whom the condition of the liver is known in each case, is examined. The images or parameter maps can then be used to form corresponding value tuples, which can be transferred as reference value tuples into the parameter space where they then form clusters with other reference value tuples according to the condition of the liver cluster.

In this context, characterization or classification can be performed, for example, according to the distance of the value tuple from the clusters. In the simplest case, a Euclidean distance in the respective parameter space can be used as the measure of the distance. In this context, the distance to a cluster can be defined, for example, as the distance to a point characterizing the cluster or a collective position of the cluster, for example the center point or focal point, the position of the main axes of the point cloud of the cluster etc. Alternatively, it is also possible to determine a distance to the closest edge of a cluster. The current value is then assigned to one cluster or the other according to the distance.

It is also possible to combine the aforementioned methods. For example, it is possible first to determine clusters of reference value tuples and then to use these clusters to determine the boundary hyperplanes, for example as boundary lines between the clusters assigned to the different classes.

The method according to the invention can also be used to construct a machine learning system. For example, starting with an initial base of reference value tuples, first a classification of the liver of a patient could be performed. This result is then added to the reference value tuples, wherein this is preferably in particular performed when the result of the classification has been reconfirmed by other diagnostic methods. This improves the probability of correct suggested characterizations or suggested classifications being output still further.

As noted above, it is possible to form a common value tuple for the region of interest. For example, a mean $T_1$ value or the reciprocal value thereof and correspondingly a mean $T_2$ or $T_2^*$ value or the corresponding reciprocal value could be determined for all image points in the region of interest and these could then be used as attributes in the value tuple for the region of interest. However, it is also possible for a plurality of value tuples to be determined for the region of interest of the liver, for example point-by-point from the $T_1$ maps and $T_2$ or $T_2^*$ maps, and for these value tuples to be transferred into the parameter space. As a value-tuple group in the multidimensional parameter space, these value tuples can then be considered to be a type of point cloud.

In this context, characterization, in particular classification, can be performed by making a check is performed to determine the positions at which the majority of the value tuples in this value-tuple group are located or which proportion is located in which region within the multidimensional parameter space. In particular, this could also enable the performance of a type of "intermediate class" or the afore-mentioned quantitative gradual classification, for example when a large proportion of the value tuples in such a value-tuple group is located in a first spatial region relative to a hyperplane indicative of a first class and other values tuples in this value-tuple group are located in another spatial region indicative of another class.

The characterization or classification can be performed on the basis of a collective position of the value-tuple group in the parameter space, for example, in that this value-tuple group then determines a geometrical center point, a focal point, the location of the main axes of the point cloud etc. and information for the characterization or classification is obtained from the position and/or orientation.

The region of interest can be only a small region within the liver, for example a box specified in advance by the physician performing the examination. Then, no segmentation of the liver is necessary, but then the entire liver tissue is not taken into account. Therefore, in a preferred variant the region of interest substantially includes the entire liver. Here, the term "substantially" should be understood as meaning the inclusion of all the image points in the region of interest which are identified in a segmentation generated by means of a usual method apart from, for example, insignificant boundary regions which may have been incorrectly assigned to the liver during the segmentation for example.

DESCRIPTION OF THE PREFERRED EMBODIMENTS

Figure 1:
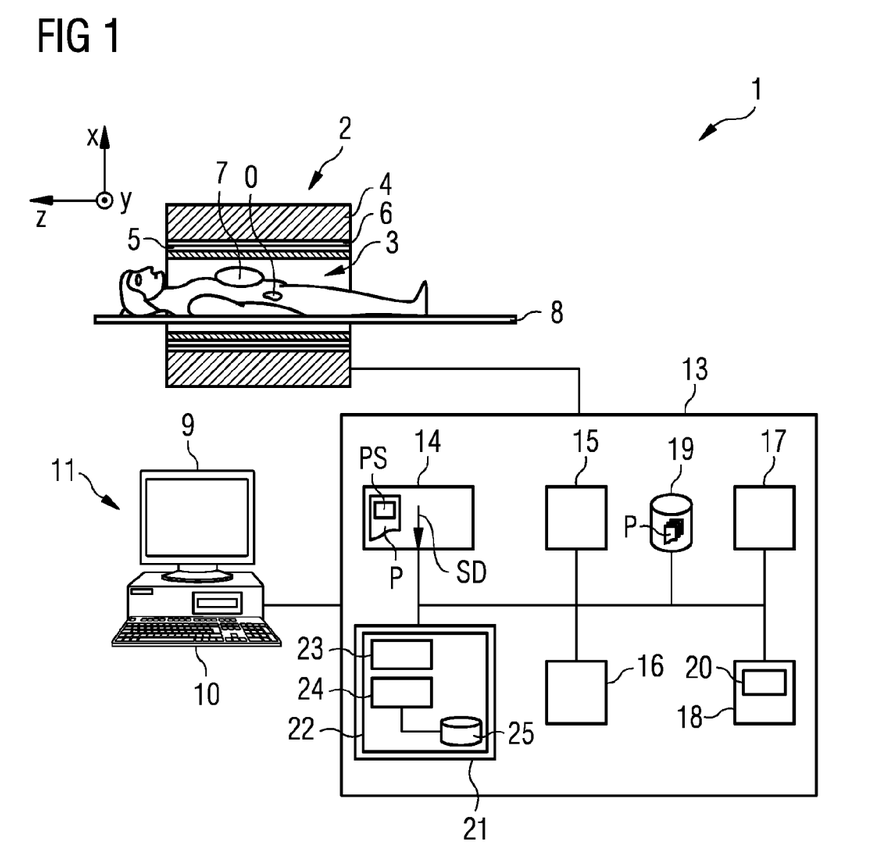
FIG. 1 schematically illustrates a magnetic resonance imaging system according to one exemplary embodiment of the invention.

FIG. 1 is a schematic illustration of a magnetic resonance imaging apparatus 1. It includes the actual magnetic resonance scanner 2 with an examination chamber 3 or patient tunnel in which a patient or test subject is positioned on a bed 8. The actual examination object O, the liver, is located in the body of the patient or test subject.

The magnetic resonance scanner 2 is typically equipped with a basic field magnet 4, a gradient coil arrangement 6 and an RF transmission antenna 5 and a RF reception antenna 7. In the exemplary embodiment depicted, the RF transmission antenna system 5 is a whole-body coil permanently installed in the magnetic resonance scanner 2, the RF reception antenna 7 is formed by local coils to be arranged on the patient or test subject (in FIG. 1 only symbolized by an individual local coil). In principle, however, it is also possible for the whole-body coil to be used as an RF reception antenna and the local coils as an RF transmission antenna as long as these coils can in each case be switched to different operating modes. The basic field magnet 4 is typically designed so as to generate a basic magnetic field in the longitudinal direction of the patient, i.e. along the longitudinal axis of the magnetic resonance scanner 2 extending in the z direction. The gradient coil arrangement 6 typically includes individually controllable gradient coils in order to be able to activate gradients in the in x, y or z directions independently of one another. The magnetic resonance scanner 2 also contains shim coils (not shown), which can be embodied conventionally.

The MR scanner 2 shown in FIG. 1 is a whole-body system with a patient tunnel into which a patient can be completely introduced, In principle, however, the invention can also be used in other MR systems, for example with a laterally open C-shaped housing. The only essential factor is that it is possible to prepare appropriate images of the liver O.

The MR apparatus 1 furthermore comprises a central control computer 13 that is used to control the MR apparatus 1. This central control computer 13 includes a sequence controller 14 that controls the sequence of radio-frequency pulses (RF pulses) and gradient pulses in dependence upon a selected pulse sequence PS or a sequence of multiple pulse sequences to acquire a number of slices in a volume region of interest of the examination object during a scanning session. Such a pulse sequence PS can be specified and parameterized in a scan or control protocol P. Different control protocols P for different scans or scanning sessions are typically stored in a memory 19 and can be selected by an operator (and optionally changed if necessary) and then used to carry out the scan. In the present case, the control computer 13 contains pulse sequences for the acquisition of the raw data for the determination of the $T_1$ values or reciprocal RI values thereof and the $T_2$ or $T_2^*$ values or the reciprocal $R_2$ or $R_2^*$ values thereof required according to the invention (as is typically already the case with standard scans) and optionally further values, such as fat values, texture, etc.

To emit the individual RF pulses of a pulse sequence PS, the central control computer 13 has a radio-frequency transmitter 15 that generates and amplifies the RF pulses and feeds them into the RF transmission antenna 5 via a suitable interface (not shown in detail). To control the gradient coils of the gradient coil arrangement 6 in order to activate the specified pulse sequence PS suitably, the control computer 13 has a gradient interface 16. It could also be possible for the shim coils to be activated via this gradient interface 16 since the gradient coils are used by setting the DC offset currents for shimming the $B_0$-Felds (namely for compensating the linear portion of the field distortions). The sequence controller 14 communicates with the radio-frequency transmitter 15 and the gradient system interface 16 in a suitable way, for example by emitting sequence control data SD to execute the pulse sequences PS.

The control computer 13 also has a radio-frequency receiver 17 (which likewise communicates with the sequence controller 14 in a suitable manner) in order to receive magnetic resonance signals within the readout window specified by the pulse sequence PS and thus to acquire the raw data.

A reconstruction processor 18 accepts the acquired raw data and reconstructs therefrom magnetic resonance image data, i.e. in particular the $T_1$-weighted images (or $T_1$ maps) or reciprocal $R_1$ maps thereof and the $T_2$ or $T_2^*$-weighted (or $T_2$ or $T_2^*$ maps) or the reciprocal $R_2$ or $R_2^*$ maps thereof. This reconstruction is performed on the basis of parameters, which can be specified in the respective scan or control protocol P. This image data can then be stored in a memory 19.

The details of how suitable raw data are acquired by the irradiation of RF pulses and the activation of gradient pulses, and MR images or parameter maps reconstructed therefrom, are known to those skilled in the art and thus need not be explained in further detail here.

Here, the compilation of the images or parameter maps required in the further method and optionally also an evaluation of the raw data to identify the higher-ranking parameters, such as fat values, texture values of the region of interest etc., are performed in a parameter map compilation processor 20 of the reconstruction processor 18.

All these values can then be sent to an evaluation computer 21, which here also includes the characterization processor 22, here specifically a classification processor, for the method according to the invention. In principle, the parameter map compilation processor 20, which is depicted in FIG. 1 as part of the reconstruction processor 18, can also be part of the evaluation computer 21 or classification processor 22. In the example shown, it is assumed without restricting the generality that the characterization of the liver tissue is performed in the form of a classification.

Here, a (software) module of this classification processor 22 is a data conversion unit 23, which analyzes the parameter maps and forms the value tuples therefrom and then transmits these into the multidimensional parameter space. For example, here a mean $T_1$ value, a mean $R_2^*$-value, a fat value FF for the fat content etc. within the region of interest ROI of the liver O are formed and the value tuple for this region of interest ROI formed therefrom and then transferred into the parameter space. In this context, the determination of the mean values can be performed such that, first, the values for the individual image points in the region of interest are determined and then a mean value is formed on the basis of these individual values.

Alternatively, as described it is also possible for separate value tuples to be formed for individual image points and/or regions and transferred into the parameter space.

Subsequently, a classifier 24 (as a further software module) then performs the actual classification, as will be explained later in more detail with reference to FIGS. 3 to 5. The infotmation required for this on the location of the boundary hyperplanes and/or the different clusters of reference tuples can, for example, be stored in a memory 25 to which the classifier 24 has access.

The central control computer 13 can be operated via a terminal 11 with an input unit 10 and a display unit 9 via which the entire MR apparatus 1 can hence be operated by an operator. It is also possible for MR images to be displayed on the display unit 9, and the input unit 10, optionally in combination with the display unit 9, can be used to plan and start measurements and in particular select and optionally modify control protocols P.

Here, it is also possible for results of the automatic classification to be presented, for example as specific suggested classifications, which can be accepted or rejected by the person tasked with performing the examination. To this end, it is also possible to display the parameters spaces used by the display 9, particularly when a two-dimensional parameter space or three-dimensional parameter space is involved, as is the case in FIGS. 3 to 5.

The MR apparatus 1 according to the invention and its control computer 13 can also have further components, not shown in detail here, but typically present in systems of this kind, such as a network interface in order to connect the entire system with a network and to enable the exchange of raw data and/or image data or parameter maps but also further data, such as patient-relevant data or control protocols.

Figure 2:
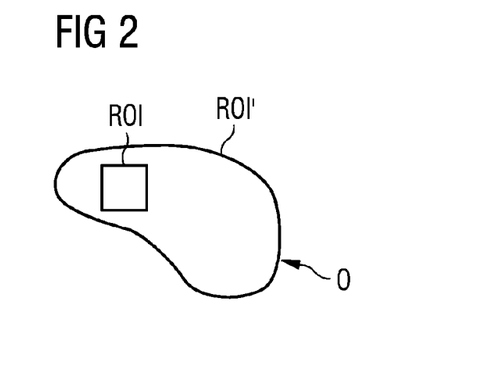
FIG. 2 schematically shows a liver for determining the region of interest.

The image points taken into account during the evaluation—i.e. for the spatial region of the liver tissue for which such a suggested classification is to be compiled—depend upon which region of interest is defined. As depicted in FIG. 2 a region of interest ROI can be defined in the form of a box or the like if, for example, a classification is only to be performed for a specific region of the liver. This can take place, for example, by the liver O or a region of the body comprising the liver O being displayed in the form of two or three-dimensional image data on the display unit 9 and the examiner then enters coordinates in order to set a corresponding box or draws this box using a mouse or similar graphical tools. However, instead of a box, it is also possible to enter any other shape. If classification of the entire liver tissue of the liver is desired, ultimately the entire liver O is the region of interest ROI'. To identify the tissue associated therewith, it is possible to perform manual segmentation, i.e. with the use of the user interface, by the boundary lines being drawn therein, for example in the image data, or automatic segmentation.

When the region of interest ROI, ROI' has been defined, the image points can be evaluated as described above in order to form the desired value tuples, which are then entered in the parameter space for the further classification. This is shown in FIG. 3 in a very simple example. Here, the parameter space PR is only two-dimensional, wherein, the $R_2^*$ value is shown in $s^{-1}$ along one coordinate axis, here the abscissa, and the $T_1$-relaxation time in ms along the other coordinate, here the ordinate. Three straight lines are drawn in this two-dimensional parameter space PR as boundary hyperplanes H1, H2, H3, wherein these straight lines overall divide four regions from one another within the parameter space PR. Each one of these regions is assigned its own class which is assigned to a specific fibrotic condition of the liver tissue from which the value tuple originates. The boundary hyperplanes H1, H2, H3 or the individual regions for the individual classes are defined with the aid of reference value tuples RT originating from liver tissue from livers for which the degree of fibrosis is known. Then, for the current examination, it is only necessary to define the position of the value tuple T belonging to the liver to be examined and it is hence very easy to define the correct class.

Figure 3:
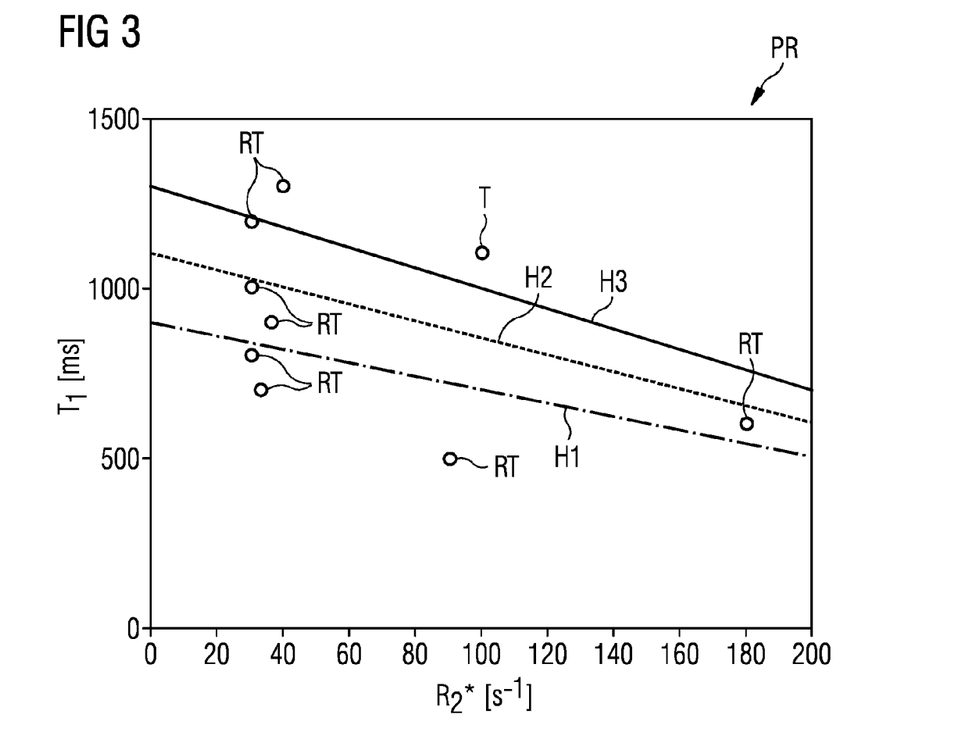
FIG. 3 shows an example of a possible classification in a two-dimensional parameter space.

It should be noted that the depiction in FIG. 3 is only a schematic representation intended to demonstrate the principle and neither the values nor the boundary hyperplanes H1, H2, H3 are based on medical data. In particular, a significantly higher number of reference value tuples is used in order to define the boundary hyperplanes H1, H2, H3. The boundary hyperplanes can also consist of curved lines or surfaces.

As mentioned, preferably further values are also added to the value tuple. An advantageous further attribute in the value tuple is a fat value or a fat portion FF, which can be defined in %.

Figure 4:
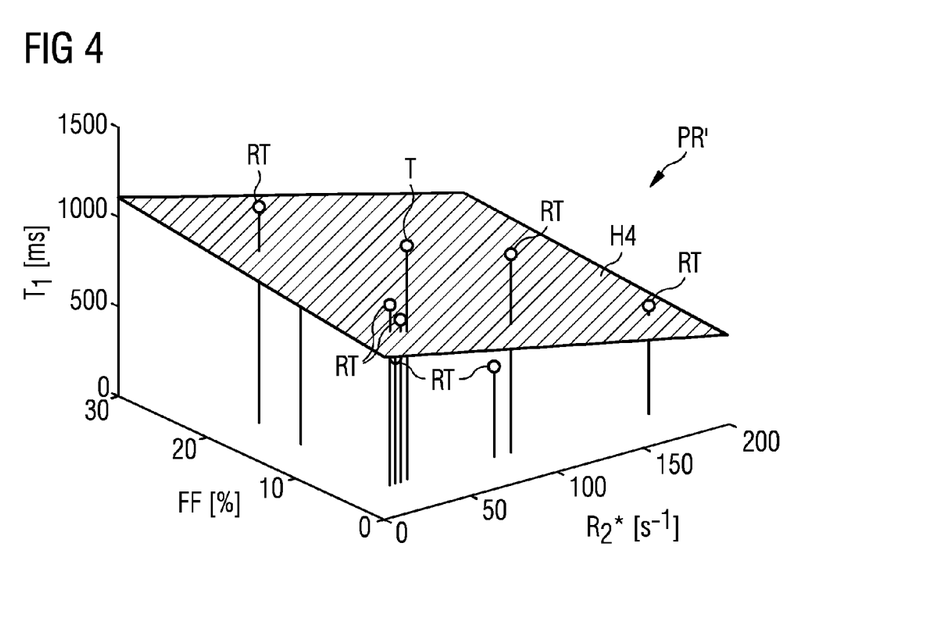
FIG. 4 shows an example of a possible classification in a three-dimensional parameter space.

FIG. 4 is a schematic representation of such a three-dimensional parameter space PR' with which the $T_1$ relaxation time is again shown in ms over the fat value FF in % and the reciprocal $T_2^*$ relaxation time, i.e. the $R_2^*$-value, is shown in $s^{-1}$.

Here, once again reference value tuples RT were used to select a suitable hyperplane H4 in order to divide the parameter space PR' into different regions assigned to specific classes. In the simplest case, as depicted here, there is only one hyperplane H4, which divides the parameter space PR' into two regions, namely one signaling, for example, that there is no fibrosis as yet, and a further region indicative of fibrosis. This representation also only entails values and hyperplanes H4 used to elucidate the system used, but not medically substantiated values.

Figure 5:
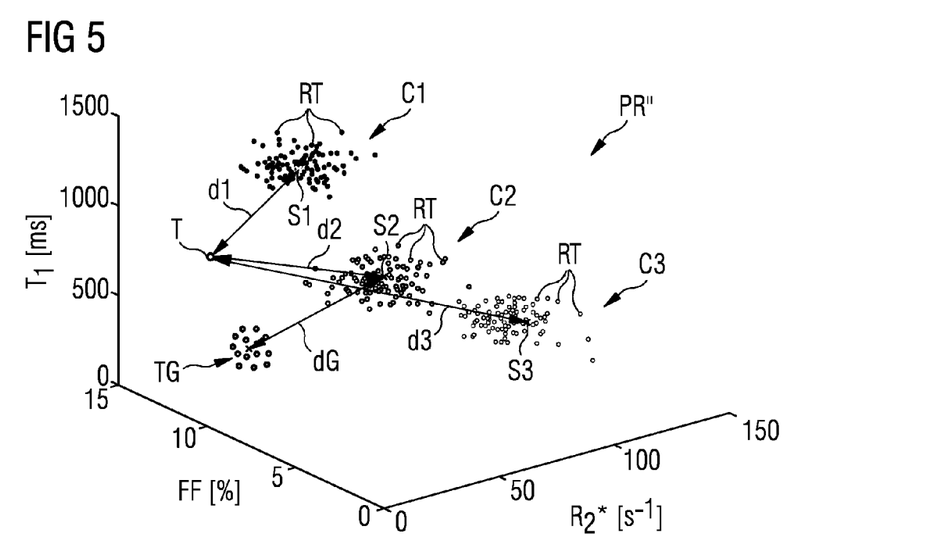
FIG. 5 shows a further example of a possible classification in a three-dimensional parameter space.

The same applies to the depiction in FIG. 5, which also shows a possibility of classification within a three-dimensional parameter space as shown in FIG. 4. This depicts how the reference value tuples RT in the space form clusters C1, C2, C3. Each of these clusters C1, C2, C3 can be assigned to a specific class representing a specific condition of the liver. The reference value tuple RT can also be determined here in that corresponding value tuples are compiled on the basis of liver tissue from patients with livers in a wide variety of pathological conditions. It is then possible for a corresponding data base to be extended within the framework of further examinations in that the value tuples for livers that have been examined and classified with the aid of the method according to the invention can be added.

These clusters could be used, for example, to form boundary hyperplanes forming the boundaries between the individual clusters. This has the advantage of enabling rapid classification with reference to the location between the boundary hyperplanes or the reference to the boundary hyperplanes and it is not necessary to retain all the reference tuples as data.

There are various possibilities for carrying out an evaluation using the point clouds of the reference value tuples RT in the clusters C1, C2, C3. One possibility consists in determining a collective value for each cluster C1, C2, C3, for example the focal point S1, S2, S3 (once again only marked symbolically in FIG. 5) of the respective point cloud, representing the respective cluster C1, C2, C3 in the parameter space. It would then be simple to determine the distance dl, d2, d3 to the respective focal point S1, S2, S3 for a value tuple T originating from the liver to be examined, wherein it is, for example, possible to use the Euclidean distance. The assignment of the value tuple T to one of the clusters C1, C2, C3 is then performed by simply accepting the cluster C1, C2, C3 with a focal point 51, S2, S3 closest to the value tuple T.

Alternatively, it possible in each case to use the distance to the closest reference tuple RT in the individual clusters C1, C2, C3. Similarly, the main axes of the clusters C1, C2, C3 could be determined and then the point of intersection of the main axes in each case form a representative point for the respective cluster C1, C2, C3. Here, a wide variety of determination possibilities is conceivable.

FIG. 5 also shows that it is in principle possible for a number of value tuples to be transmitted as a value-tuple group TG into the parameter space PR" for a liver that is currently to be examined and for the classification then to be performed on the basis of this value-tuple group TG. For example, here once again the focal point of the value-tuple group TG could be determined and a distance between the focal point of value-tuple group TG and the focal points S1, S2, S3 of cluster C1, C2, C3 determined in each case (in FIG. 5, by way of example, only the distance dG to the focal point S2 of the middle cluster C2 is depicted) in order then to perform the classification in a similar way to that described above.

The way in which the characterization, in particular classification, is ultimately performed is in particular also dependent upon which further parameters are added if, instead of a three-dimensional parameter space, a four- or five-dimensional space is used, how the position of the individual value tuples in this parameter space is depicted and how effectively it is possible to demarcate the individual regions from one another.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for automatic characterization of liver tissue in a region of interest of a liver, comprising:
    providing a processor with at least one value tuple of a region of interest of the liver of a subject, said value tuple comprising a $T_1$ value determined from a magnetic resonance image of the region of interest or a reciprocal of said $T_1$ value, and a $T_2$ value determined from said image or a $T_2^*$ value determined from said image or a reciprocal of said $T_2^*$ value, and a fat value;
    in said processor, transferring the value tuple into a multi-dimensional parameter space;
    in said processor, generating a characterization of liver tissue in the liver from a position of the value tuple in the multi-dimensional parameter space; and
    making an electronic signal representing said characterization of the liver available as an output from the processor.

2. A method as claimed in claim 1 comprising, in said processor, characterizing the liver tissue based on the position of the value tuple in the parameter space with reference to a boundary hyperplane of the parameter space.

3. A method as claimed in claim 1 comprising characterizing the liver tissue on the basis of the position of the value tuple in the parameter space with reference to at least one cluster of reference value tuples in the parameter space.

4. A method as claimed in claim 1 comprising providing the processor with a plurality of value tuples of the region of interest of the liver, and transferring the plurality of value tuples into the multi-dimensional parameter space as a value-tuple group, and characterizing the liver tissue based on a collective position of the value-tuple group in the parameter space.

5. A method as claimed in claim 1 wherein said region of interest includes an entirety of the liver.

6. A method as claimed in claim 1 comprising providing the processor with said at least one value tuple by:
    acquiring magnetic resonance data from said region of interest of the liver;
    reconstructing an image of the liver from said magnetic resonance data, said image comprising voxels in said region of interest of the liver; and
    determining said $T_1$ value or the reciprocal value thereof, said $T_2$ value, or said $T_2^*$ value or said reciprocal value thereof, from said voxels in said region of interest of the liver in said image.

7. A characterization computer for automatic characterization of liver tissue in a region of interest of a liver of a subject, said computer comprising:
    an input interface that receives a magnetic resonance image of the liver tissue in said region of interest;
    a processor configured to determine at least one value tuple from said region of interest, said value tuple comprising a $T_1$ value or a reciprocal of said at least one $T_1$ value, and a $T_2$ value or a $T_2^*$ value or a reciprocal of said $T_2^*$ value, and a fat value; said processor being configured to transfer the value tuple into a multi-dimensional parameter space;
    said processor being configured to generate a characterization of liver tissue in the liver from a position of the value tuple in the multi-dimensional parameter space; and
    said processor being configured to make an electronic signal representing said characterization of the liver available as an output from the processor.

8. A magnetic resonance (MR) apparatus comprising:
    an MR data acquisition scanner;
    a control computer configured to operate the MR data acquisition scanner to acquire MR data from a region of interest of a liver of a subject;
    a reconstruction computer configured to reconstruct an image of the region of interest of the liver from said MR data;
    a processor configured to acquire at least one value tuple of the region of interest of the liver that a $T_1$ value determined from said image, or a reciprocal of said $T_1$ value, and a $T_2$ value determined from the image or a $T_2^*$ value determined from said image or a reciprocal of said $T_2^*$ value, and a fat value;
    said processor being configured to transfer the value tuple into a multi-dimensional parameter space;
    said processor being configured to characterize liver tissue in the liver in said region of interest based on a position of the value tuple in said multi-dimensional parameter space; and
    said processor being configured to generate an electronic signal representing said characterization of the liver tissue in the region of interest and to emit said electrical signal from said processor.

9. A non-transitory, computer-readable data storage medium encoded with programming instructions, said storage medium being loaded into a computer of a magnetic resonance (MR) apparatus, and said programming instructions causing said computer to:
    determine at least one value tuple of a region of interest of the liver of a subject, said value tuple comprising a $T_1$ value determined from a magnetic resonance image of the region of interest or a reciprocal of said $T_1$ value, and a $T_2$ value determined from said image or a $T_2^*$ value determined from said image or a reciprocal of said $T_2^*$ value, and a fat value;
    transfer the value tuple into a multi-dimensional parameter space;
    generate a characterization of liver tissue in the liver from a position of the value tuple in the multi-dimensional parameter space; and
    make an electronic signal representing said characterization of the liver available as an output from the computer.

* * * * *